United States Patent
Moritz et al.

(10) Patent No.: US 7,481,981 B2
(45) Date of Patent: Jan. 27, 2009

(54) APPARATUS FOR THE ESTERIFICATION OF A FATTY ACID

(75) Inventors: Peter Moritz, Wiesendangen (CH); Peter Faessler, Singapore (SG); Claudia von Scala, Zurich (CH); Oliver Bailer, Winterthur (CH)

(73) Assignee: Sulzer Chemtech AG, Winterthur (CH)

( * ) Notice: Subject to any disclaimer, the term of this patent is extended or adjusted under 35 U.S.C. 154(b) by 274 days.

(21) Appl. No.: 11/405,059

(22) Filed: Apr. 17, 2006

(65) Prior Publication Data

US 2006/0199971 A1    Sep. 7, 2006

Related U.S. Application Data

(62) Division of application No. 10/706,449, filed on Nov. 12, 2003, now Pat. No. 7,091,367.

(30) Foreign Application Priority Data

Nov. 28, 2002    (EP)    ................................. 02406034

(51) Int. Cl.
*B01J 19/00* (2006.01)
*C11C 3/00* (2006.01)

(52) U.S. Cl. ........................ 422/131; 422/190; 422/211; 422/213; 554/170

(58) Field of Classification Search ................. 554/170; 422/190, 211, 213, 131, 132
See application file for complete search history.

(56) References Cited

U.S. PATENT DOCUMENTS

| | | | | |
|---|---|---|---|---|
| 5,349,075 | A | * | 9/1994 | van den Berg et al. ...... 554/170 |
| 5,616,735 | A | * | 4/1997 | Hunt .......................... 549/413 |
| 7,091,367 | B2 | * | 8/2006 | Moritz et al. ............... 554/170 |

* cited by examiner

*Primary Examiner*—N. Bhat
(74) *Attorney, Agent, or Firm*—Francis C. Hand; Carella, Byrne, Bain et al

(57) ABSTRACT

The apparatus for the esterification of a fatty acid F includes a column with a packing. In addition to functioning as a catalytic reactor, the packing functions as a stripping section. A heteregenous catalysis of a fatty acid is carried out with an alcohol used in the same molar ratio or in excess. A gaseous alcohol-rich counter-flow is produced in a sump of the column by vaporization. Water is removed from the reaction zone by means of the counter-flow acting as a stripping gas. The loaded stripping gas is at least partially liquefied at the head of the column. The head product is separated into a water-rich fraction as well as an alcohol-rich fraction. The alcohol-rich fraction is returned to the process as a starting material for the esterification and for the production of the stripping gas.

3 Claims, 2 Drawing Sheets

APPARATUS FOR THE ESTERIFICATION OF A FATTY ACID

This application is a divisional application of Ser. No. 10/706,449, filed Nov. 12, 2003 now U.S. Pat. No. 7,091,367, which claims foreign priority to EPO 0240634.5.

This invention relates to an apparatus for the production of fatty acid ester by means of a heterogeneous catalysis.

According to a customary method, in order to esterify a fatty acid, a pre-determined amount of the fatty acid is esterified in batches. In this, the fatty acid is placed in a heatable container with a stirring mechanism and heated to approximately 100° to 250° C. A catalyst is added and the esterification is carried out at a temperature which is kept constant, and with a constant infeed of alcohol. A stream of vapor from the container is led into a separating column, in which water that is released during esterification is separated from the co-vaporised alcohol. The water can be thus removed from the process, by which means the conversion is improved. On completion of the esterification process, the remainders of alcohol and water are removed by further heating.

A continuous method for the esterification of fatty acids is described in U.S. Pat. No. 6,069,261, in which a "permanent" auxiliary gas is used for removing water continuously. An auxiliary gas of this kind, which is hydrogen or nitrogen for example, does not enter into a chemical reaction with reactants of the esterification.

The object of the invention is to provide an apparatus for the esterification of fatty acids, which can be carried out continuously and in which no auxiliary gas such as hydrogen or nitrogen has to be used.

Briefly, the invention an apparatus that employs a method for the esterification of a fatty acid F that is carried out in a column with a one or multi-part packing.

In addition to functioning as a reactor, the packing has the function of a stripping section. This stripping section is formed as a reaction zone, at least in an upper part of the packing, in which a heterogeneous catalysis of the fatty acid F is carried out with an alcohol A used in the same molar ratio or in excess.

In addition, a gaseous alcohol-rich counter-flow is produced in a sump of the column by vaporisation. Water is removed from the reaction zone by means of the alcohol rich counter-flow acting as a stripping gas.

The loaded stripping gas is at least partially liquefied at the head of the column. The head product is separated into a water-rich fraction as well as an alcohol-rich fraction. The alcohol-rich fraction is returned to the process as a starting material for the esterification and for the production of the stripping gas.

In particular, the apparatus includes a column with a part of a packing for carrying out the heterogeneous catalysis. The packing includes porous catalyst supports and flow channels for the stripping gas between the catalyst supports, wherein, on carrying out the method in the pores of the catalyst supports, the mixture to be treated forms a downwardly directed flow of liquid, the stripping gas forms an upwardly directed flow and the liquid phase is in direct contact to the gaseous phase, so that a material exchange can take place.

These and other objects and advantages of the invention will become more apparent form the following description taken in conjunction with he accompanying drawings wherein.

The present description applies to the manufacture of a fatty acid ester E, for example a fatty acid isopropyl ester, which boils more easily than the corresponding fatty acid F.

The starting products of the process in accordance with the invention are an alcohol A and a fatty acid F.

Figures 1, 2:
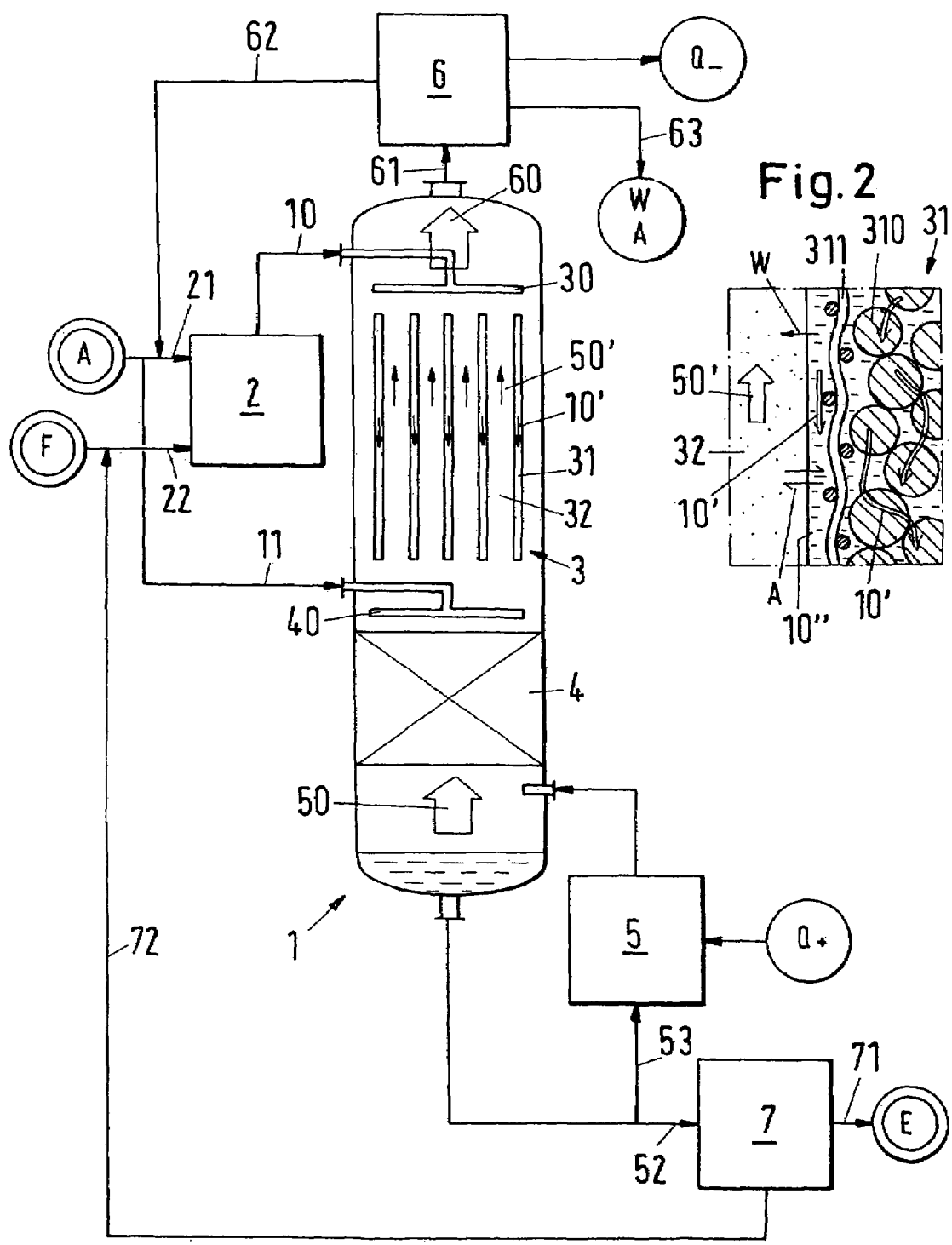
FIG. 1 illustrates an apparatus with a column in which a catalytic reaction zone is arranged that is used for carrying out the method in accordance with the invention.
FIG. 2 illustrates a section of the catalytic reaction zone in the column of FIG. 1.

Referring to FIG. 1, the column 1 contains a packing part 3 which defines a catalytic reaction zone in which an esterification takes place by means of a heterogeneous catalysis.

An alcohol A is supplied via a line 21 to a pre-reactor 2 and a fatty acid F is supplied to pre-reactor 2 via a line 22. The mixer 2, in turn, forms a mixture of the fatty acid F and the alcohol A that is then fed via a line 10 and a distributor 30 in the column to the packing 3 in the column 1.

Alcohol A is also delivered via a line 11 and a distributor 40 in the column to a second packing part 4 arranged under the packing part 3.

The packing consisting of the two parts 3 and 4, in addition to functioning as a reactor, functions as a stripping section. The alcohol A is used in the same molar ratio or in excess. Thus, alcohol A that is delivered into the sump can be vaporised so that a gaseous alcohol-rich counter-flow 50 can be produced. This gaseous counter-flow 50 is then used as a stripping gas 50' in the reaction zone defined by the upper packing 3 to remove water W from the reaction zone. The heat needed for the vaporisation is supplied to an apparatus 5 by heating a branch flow 53 (heat supply $Q_+$). Water W and also alcohol A is already taken up by the stripping gas 50 in the lower part 4 of the stripping section out of the liquid mixture which emerges from the reaction zone 3.

The loaded stripping gas (arrow 60) is delivered via a line 61 to an apparatus 6 above the column 1 wherein the loaded gas is at least partially liquefied (heat extraction Q−) and separated into two fractions 62 and 63. The fraction 63 of the head product that is water rich and has a proportion of water W of 80% by weight for example. The other fraction 62 is alcohol rich and contains 95%-98% by weight of alcohol A for example. This alcohol rich fraction is returned to the input line 21 for re-cycling in the process as a starting material for the esterification and to produce the stripping gas 50. The separation of the head product into the alcohol-rich fraction 62 and the water-rich fraction 63 can be undertaken for example by means of a membrane process, pervaporation, by means of a phase separator or by means of a distillation column.

The alcohol A which is fed in via the lower distributor 40 is vaporised on the packing 4 and thus contributes to the stream of the stripping gas 50. The necessary heat of vaporisation is given up by the stripping gas 50, which is brought into an overheated state in the sump by vaporisation.

In the example shown, the catalytic reaction zone 3 is made up of vertical layers 31 and flow passages 32 for the stripping gas 50'. A mixture 10', which contains the starting materials A and F, flows into and onto the layers 31.

Details of the reaction zone 3 are illustrated in FIG. 2, namely a border region between a flow passage 32 with the stripping gas 50' and a layer 31, which contains a granulated material 310 of a catalyst. A fabric 311 of durable material forms pockets in which the granulated material 310 is enclosed. The mixture 10' flows inside one pocket and on the exterior side of the fabric 311, inside the pocket with meandering flow paths and outside as a trickle film.

Water W enters into the stream of the stripping gas 50' through the surface of the trickle film 10", because a relatively small partial pressure of the water W is present in this.

Alcohol A is transported in both directions through the surface of the trickle film 10". Suitable packings for the reaction zone 3 are described in EP-A-0 396 650 and in EP-A-0 631 813.

The starting materials A and F are already partially reacted together to advantage in the pre-reactor 2, wherein 10 to 30% of the fatty acid F is converted to ester E. Thus, a mixture of alcohol A, fatty acid F, ester E and water W flows into the column 1 through the line 10. Then, a further 20% to 70% of the fatty acid F is converted in the reaction zone 3.

Figure 3:
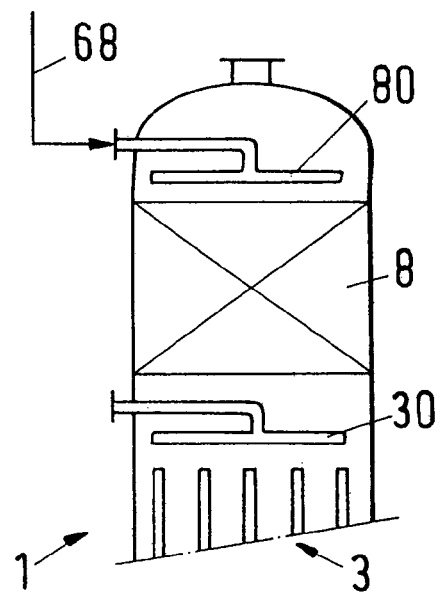
FIG. 3 illustrates a head region of a preferred embodiment of the column.

Referring to FIG. 3, a further packing 8 and a distributor 80 are advantageously built into the column 1 above the stripping section 3, 4 and a part 68 of the returned alcohol-rich fraction 62 is delivered into the packing 8 via the distributor 80. Fatty acid F, which carries the stripping gas 60, is caught in this packing 8 with the retured alcohol.

Referring to FIG. 1, the sump is connected via a line 51 to a plant 7 for cleaning and concentration so that an intermediate product, namely a mixture, that contains a fatty acid ester can be extracted from the sump via the line 51 and fed to a part of the plant 7 for cleaning and concentration. In this respect, the intermediate product obtained in the column 1 still contains remains of the starting products as well as impurities. The intermediate product is further treated in a separating column of the part of the plant 7, so that eventually a fatty acid ester E can be obtained, the purity of which is at least 99% by weight. The cleaned fatty acid ester E product is extracted via a line 71. A remainder of fatty acid F separated in the separating column is returned via a line 72 to the line 22 for recycling in the process Referring to FIG. 4, wherein like reference characters indicate like parts as above, the part of the plant 7 for cleaning the fatty acid that has been produced includes a relaxation vaporiser 9, in which the intermediate product of the line 52 liberates a greater part of the remaining alcohol A in vapor form. This alcohol-rich vapor is led away via a line 92 and can be used further for the esterification. The alcohol-low mixture is led into a separating column 70 through a line 91. The extraction of the cleaned ester E (line 71) takes place there.

The head product which can be extracted from a condenser 75 through a line 76 contains alcohol A and volatile impurities, in particular air. Fatty acid F (line 72) and not easily volatised impurities (line 74) can be extracted from the sump to which heat is supplied using a heating circuit 73. This part of the plant 7 can also be arranged as a distillation column.

Figure 4:
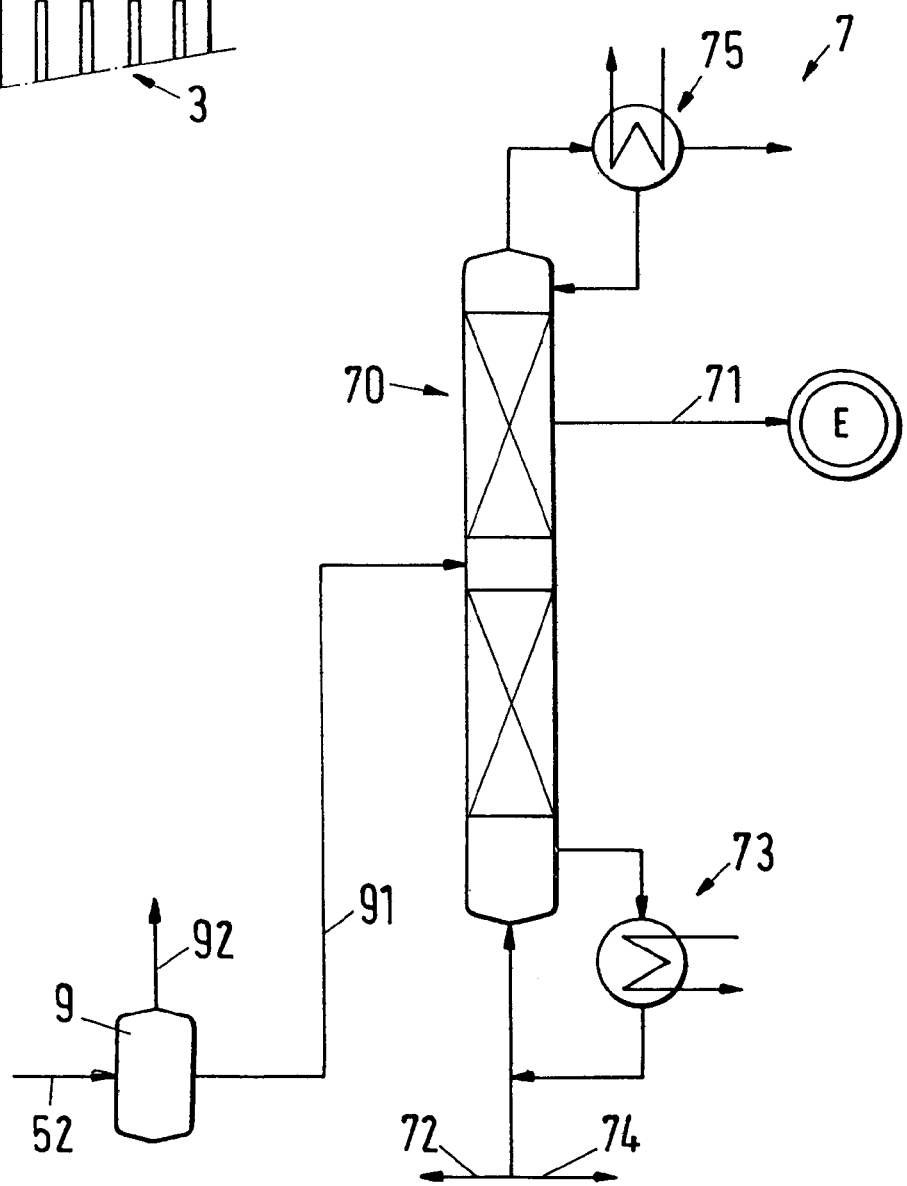
FIG. 4 illustrates a part of an apparatus for cleaning the fatty acid ester that has been produced.

Referring to FIG. 4, a different separating process may be used when the fatty acid ester E boils at a lower temperature than the corresponding fatty acid F. In the case of fatty acids that are esterified with higher alcohols (for example 2-ethyl-hexanol), inverse ratios apply with regard to the cleaning in the part of the plant 7. The fatty acid ester is received in the sump of the separating column 70 and has to be worked up further (not illustrated). Fatty acid and remaining alcohol, which can be extracted in the head from the separating column 70, are returned to the process.

The following starting materials can be used as fatty acid F or alcohol A for the esterification for the fatty acid F: one of the C12-, C14-, C16-, C18-, C18'- or C18"-fatty acids, namely lauric acid, myristic acid, palmitic acid, stearic acid, oleic or linoleic acid);

for the alcohol A: one of the alcohols methanol, ethanol, n-propanol, isopropanol, n-butanol, isobutanol or 2-ethyl-hexanol.

An ion exchange resin or an inorganic catalyst can be used as a catalyst, wherein the catalysts are preferably present in a strongly acid form and the ion exchange resin is preferably made macroporous. If methanol, ethanol, n-propanol, isopropanol, n-butanol or isobutanol is the alcohol A, then the catalyst—in this case an ion exchange resin—must be able to be used at temperatures between 120° C. and 140° C.; and must only lose activity moderately in this temperature range. If 2-ethyl-hexanol is the alcohol A, then the catalyst—in this case an inorganic catalyst—has to be usable at temperatures of 150° to 230° C.

In the following, a few values of method parameters will be given for the esterification of palmitic acid (PA) with isopropanol (IPA).

For the starting materials A=IPA and F=PA, a respective purity of 95% and 98% (% by weight) is preferred. However, other values are also possible, namely, in the ranges 88%-100% for IPA and 95%-100% for PA.

The pre-reactor 2 is operated at 100° C. and 2 bar. The pre-reactor 2 can however also be operated at temperatures of up to 140° C. and at correspondingly higher pressures of up to 4 bar. As a rule, differing amounts of IPA are fed in through the lines 21 and 11. The ratio of IPA (line 21) to IPA (line 11) is in the range of 1 to 4, and preferably 2.5. The head pressure in the column 1 amounts to 2 to 5 bar and correspondingly the temperature in the reaction zone 3 amounts to 120° C. to 140° C.

The intermediate product (line 53) is heated up to a temperature of between 170° C. and 200° C. in the heating apparatus 5 and can, however, also be heated more to 250° C.

A stripping gas 60 (FIG. 1) is present in the head of the column above the packing 8 (FIG. 3), which has a temperature between 115° C. and 140° C. and which contains 5% to 12% water W. The intermediate product in the line 53 contains 50% to 80% ester and 2% to 10% IPA.

A relaxation vaporisation 9 is carried out at 1 bar and 160° to 210° C. In this, the proportion of IPA is decreased to about 0.5%. The separating column 70 is operated at 15 to 40 mbar. The temperature in the condensser 75 is reduced to a value between 80° and 100° C. and a temperature between 220° C. and 240° C. is produced in the heating circuit 73. The upper limit of this temperature can also be 250° C.

Two examples of esterification in accordance with the invention which were obtained in pilot experiments are given in the following.

EXAMPLE 1

The exterification of palmitic acid with isopropanol was continually carried out in a column at atmospheric pressure under the following conditions:
Reaction column:
inner diameter: 50 mm.
Enrichment section and stripping section: Sulzer packing BX
Reaction zone: Katapak-S/ filled with strongly acidic ion exchanger, which is stable at temperatures of up to 140° C.
Feed streams:
palmitic acid (feed 1): 2.16 kg/h
isopropanol (feed 2): 1.44 kg/h
Product streams:
head product: 1.2 kg/h—sump product: 2.4 kg/h
Operating conditions:
head pressure: 1013 mbar—return ratio: 0.2
temperature in the reaction zone: approximately 98° C.
sump temperature: 157.9° C.
Measured sump concentrations (in % by weight):
isopropylpalmitate 14.04
isopropanol: 10.61
palmitic acid: 74.5
water: 0.83

EXAMPLE 2 the same construction as in Example 1 was realised in a pressure column. In this, an already pre-activated feed was used, with which a pre-reactor could be simulated. By means of slight excess pressure, a temperature in the range of the reaction zone of approximately 140° C. was set in the reaction zone. The following operating conditions led to a significantly higher reaction conversion.

Feed streams:
feed 1: 2.3 kg/h with the following composition (in % by weight):
isopropylpalmitate: 24.3
isopropanol: 21.6
palmitic acid: 52.1
water: 2.0
feed 2: isopropanol: 1.84 kg/h
Product streams:
head product: 1-43 kg/h—sump product: 2.71 kg/h
Operating conditions:
head pressure: 5100 mbar—return ratio: 0.2
temperature in the reaction zone: approximately 140° C.
sump temperature: 192° C.
Measure sump concentration (in % by weight):
Isopropylpalmitate: 64.0
isopropanol: 7.7
palmitic acid: 28.3
water: 0.06

What is claimed is:

1. An apparatus for the production of a fatty acid ester E by means of a heterogeneous catalysis comprising
    a column;
    a fluid supply inlet in fluid connection with said column;
    a packing disposed in said column for carrying out a heterogeneous catalysis of a fatty acid and alcohol, said packing including porous catalyst supports defining flow channels therebetween for passage of a stripping gas between said catalyst supports and catalyst within said porous catalyst supports;
    a distributor for directing a downwardly directed flow of a mixture of fatty acid and alcohol onto said packing for passage through said catalyst supports in counter-flow to an upwardly directed flow of stripping gas with the mixture in direct contact with the gas to allow a material exchange to take place; and
    a sump below said packing for receiving alcohol from said packing and for generating an upward flow of stripping gas from the alcohol in said sump.

2. An apparatus as set forth in claim 1 wherein said catalyst is an inorganic catalyst in acidic form and suitable for use in a temperature range of from 150° to 230° C.

3. An apparatus as set forth in claim 1 wherein said catalyst is an ion exchange macroporous resin in acidic form and suitable for use in a temperature range of up to 140° C.

* * * * *